US 11,941,808 B2

(12) United States Patent
Chino et al.

(10) Patent No.: US 11,941,808 B2
(45) Date of Patent: Mar. 26, 2024

(54) MEDICAL IMAGE PROCESSING DEVICE, MEDICAL IMAGE PROCESSING METHOD, AND STORAGE MEDIUM

(71) Applicant: ZIOSOFT, INC., Tokyo (JP)

(72) Inventors: Shusuke Chino, Tokyo (JP); Yuichiro Hourai, Tokyo (JP)

(73) Assignee: ZIOSOFT, INC., Tokyo (JP)

( * ) Notice: Subject to any disclaimer, the term of this patent is extended or adjusted under 35 U.S.C. 154(b) by 102 days.

(21) Appl. No.: 17/651,841

(22) Filed: Feb. 21, 2022

(65) Prior Publication Data
US 2022/0270246 A1 Aug. 25, 2022

(30) Foreign Application Priority Data

Feb. 22, 2021 (JP) ................................. 2021-026627

(51) Int. Cl.
*G06T 15/08* (2011.01)
*G06T 7/00* (2017.01)

(52) U.S. Cl.
CPC ............ G06T 7/0012 (2013.01); G06T 15/08 (2013.01); *G06T 2207/30096* (2013.01); *G06T 2207/30101* (2013.01); *G06T 2210/41* (2013.01)

(58) Field of Classification Search
CPC .............. G06T 7/0012; G06T 15/08; G06T 2207/30096; G06T 2207/30101; G06T 2210/41; G06T 19/20; G06T 2219/2012; G16H 20/40; G16H 30/20; G16H 30/40; G16H 50/50; A61B 2034/105; A61B 34/10
See application file for complete search history.

(56) References Cited

U.S. PATENT DOCUMENTS

| 2006/0103670 | A1 | 5/2006 | Matsumoto | |
| 2012/0026162 | A1* | 2/2012 | Masumoto | G06T 19/00 345/419 |
| 2013/0144160 | A1* | 6/2013 | Sakuragi | A61B 6/037 600/425 |
| 2015/0063669 | A1* | 3/2015 | Wiemker | G06T 11/00 382/131 |
| 2015/0178989 | A1* | 6/2015 | Itai | G06T 15/08 382/131 |
| 2015/0196228 | A1* | 7/2015 | Akimoto | A61B 5/065 600/117 |
| 2016/0307358 | A1 | 10/2016 | Suzuki | |

(Continued)

FOREIGN PATENT DOCUMENTS

JP 4188900 B2 12/2008
JP 2016-202319 A 12/2016

(Continued)

*Primary Examiner* — Jitesh Patel
(74) *Attorney, Agent, or Firm* — Pearne & Gordon LLP

(57) ABSTRACT

A medical image processing device for visualizing an organ includes a processor. the processor is configured: to acquire volume data including the organ; to extract tubular tissues included in the organ; to designate an excision region that is a region to be excised in the organ; to determine whether or not to excise tubular tissues included in the excision region; and not to display tubular tissues to be excised in the excision region and to display tubular tissues not to be excised in the excision region on a display unit, when displaying a remaining region that is a range excluding the excision region in the organ.

10 Claims, 11 Drawing Sheets

(56) References Cited

U.S. PATENT DOCUMENTS

| | | | |
|---|---|---|---|
| 2017/0301129 A1 | 10/2017 | Seo et al. | |
| 2019/0392945 A1* | 12/2019 | Jian | A61B 6/5247 |
| 2020/0242776 A1 | 7/2020 | Nagata et al. | |
| 2020/0243184 A1* | 7/2020 | Nagata | G06T 19/00 |

FOREIGN PATENT DOCUMENTS

| | | |
|---|---|---|
| JP | 2017-189460 A | 10/2017 |
| JP | 2018-121857 A | 8/2018 |
| JP | 2020-120827 A | 8/2020 |
| JP | 2020-120828 A | 8/2020 |

\* cited by examiner

MEDICAL IMAGE PROCESSING DEVICE, MEDICAL IMAGE PROCESSING METHOD, AND STORAGE MEDIUM

CROSS-REFERENCE TO RELATED APPLICATIONS

This application is based on and claims priority under 35 USC 119 from Japanese Patent Application No. 2021-026627 filed on Feb. 22, 2021, the contents of which are incorporated herein by reference.

TECHNICAL FIELD

The present disclosure relates to a medical image processing device, a medical image processing method, and a storage medium storing a medical image processing program for causing a computer to execute the medical image processing method.

BACKGROUND

The related art discloses a technique for ligation and resection of tubular tissues including blood vessels at the time of excision of an organ. The related art discloses a medical image processing device that highlights a ligation and resection site (see JP-A-2020-120827).

In the technique of JP-A-2020-120827, the cut surface of a blood vessel can be visualized. However, partial excision of an organ, including blood vessels, is not considered.

Therefore, it is difficult to visualize a state of an organ at the time of partial excision including a state of tubular tissues such as a blood vessel.

The present disclosure has been made in view of the above circumstances and provides a medical image processing device, a medical image processing method, and a storage medium storing a medical image processing program capable of suitably visualizing a state of an organ at the time of partial excision including a state of tubular tissues in the excision region of the organ.

SUMMARY

A medical image processing device for visualizing an organ includes a processor. The processor is configured: to acquire volume data including the organ; to extract tubular tissues included in the organ; to designate an excision region that is a region to be excised in the organ; to determine whether or not to excise tubular tissues included in the excision region; and not to display tubular tissues to be excised in the excision region and to display tubular tissues not to be excised in the excision region on a display unit, when displaying a remaining region that is a range excluding the excision region in the organ.

According to the present disclosure, a state of an organ at the time of partial excision can be suitably visualized including a state of tubular tissues in the excision region of the organ.

BRIEF DESCRIPTION OF DRAWINGS

Exemplary embodiments of the present disclosure will be described in detail based on the following figures, wherein.

DETAILED DESCRIPTION

Hereinafter, embodiments of the present disclosure will be described with reference to the drawings.

First Embodiment

Figure 1:
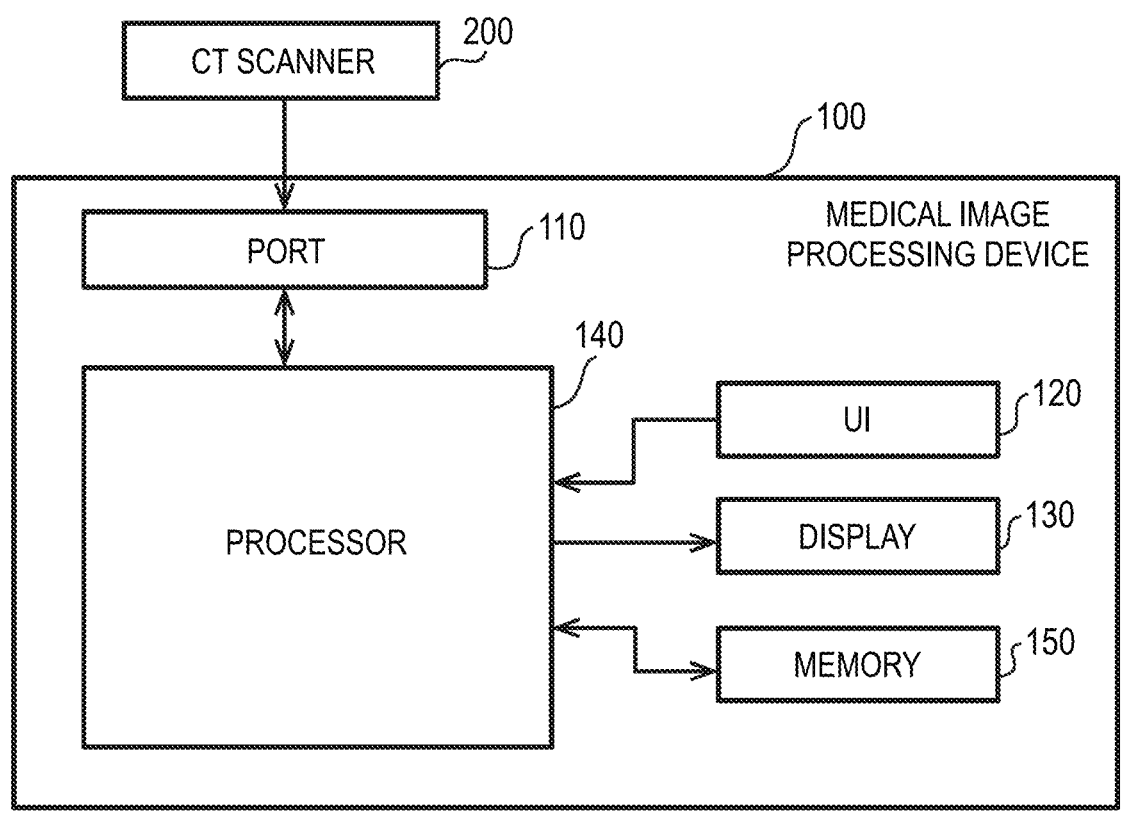
FIG. 1 is a block diagram showing a hardware configuration example of a medical image processing device according to a first embodiment.

FIG. 1 is a block diagram showing a configuration example of a medical image processing device 100 according to the first embodiment. The medical image processing device 100 includes a port 110, a UI 120, a display 130, a processor 140, and a memory 150.

A CT scanner 200 is connected to the medical image processing device 100. The medical image processing device 100 acquires volume data from the CT scanner 200 and processes the acquired volume data. The medical image processing device 100 may be composed of a PC and software mounted on the PC.

The CT scanner 200 irradiates a subject with X-rays and captures an image (CT image) by utilizing the difference in X-ray absorption by tissues in the body. The subject may include a living body, a human body, an animal, and the like. The CT scanner 200 generates volume data including information on any location inside the subject. The CT scanner 200 transmits volume data as a CT image to the medical image processing device 100 via a wired line or a wireless line. For the imaging of CT images, imaging conditions related to CT imaging and contrast conditions related to administration of a contrast medium may be considered. The contrast may be performed on the arteries and veins of the organ. The contrast may be performed multiple times at different timings depending on the characteristics of the organ.

The port 110 in the medical image processing device 100 includes a communication port, an external device connection port, and a connection port to an embedded device, and acquires volume data obtained from a CT image. The acquired volume data may be immediately sent to the processor 140 for various processing or may be stored in the memory 150 and then sent to the processor 140 for various processing when necessary. Further, the volume data may be acquired via a recording medium. Further, the volume data may be acquired in the form of intermediate data, compressed data, or sinogram. Further, the volume data may be acquired from the information from a sensor device attached to the medical image processing device 100. The port 110 functions as an acquisition unit for acquiring various data such as volume data.

The UI 120 may include a touch panel, a pointing device, a keyboard, or a microphone. The UI 120 accepts any input operation from the user of the medical image processing device 100. The user may include a doctor, a radiologist, a student, or other paramedic staff.

The UI 120 accepts various operations. For example, the UI 120 accepts operations such as the designation of a region of interest (ROI) and setting of luminance conditions in a volume data or an image based on the volume data (for example, a three-dimensional image or a two-dimensional image described later). The region of interest may include regions of various tissues (for example, blood vessels, bronchi, organs, bones, and brain). The tissues may include a lesioned tissue, normal tissue, tumor tissue, and the like.

The display 130 may include, for example, an LCD and displays various information. The various information may include a three-dimensional image or a two-dimensional image obtained from the volume data. The three-dimensional image may include a volume-rendered image, a surface rendered image, a virtual endoscopic image, a virtual ultrasonic image, a CPR image, and the like. The volume-rendered image may include a RaySum image, a MIP image, a MinIP image, an average value image, or a raycast image. The two-dimensional image may include an axial image, a sagittal image, a coronal image, an MPR image, and the like.

The memory 150 includes a primary storage device such as various ROMs and RAMs. The memory 150 may include a secondary storage device such as an HDD or an SSD. The memory 150 may include a tertiary storage device such as a USB memory or an SD card. The memory 150 stores various information and programs. The various information may include volume data acquired by the port 110, an image generated by the processor 140, setting information set by the processor 140, and various programs. The memory 150 is an example of a non-transient recording medium on which a program is recorded.

The processor 140 may include a CPU, a DSP, or a GPU. The processor 140 functions as a processing unit 160 that performs various processes and controls by executing a medical image processing program stored in the memory 150.

Figure 2:
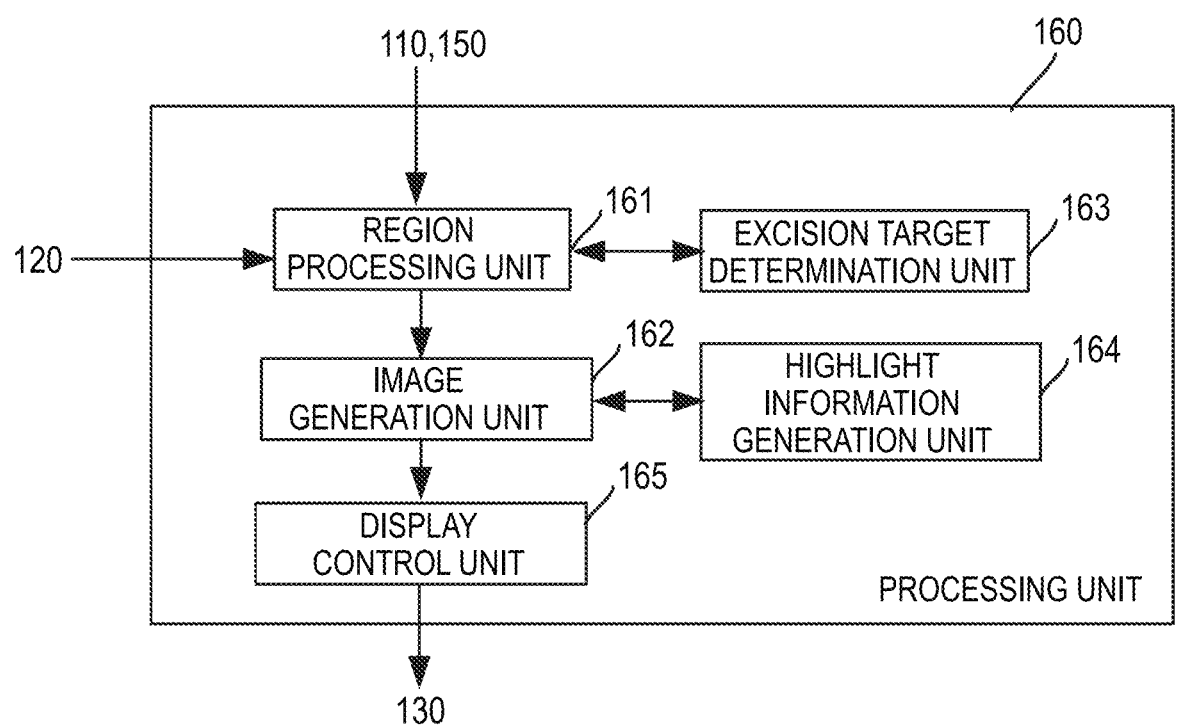
FIG. 2 is a block diagram showing a functional configuration example of the medical image processing device.

FIG. 2 is a block diagram showing a functional configuration example of the processing unit 160.

The processing unit 160 includes a region processing unit 161, an image generation unit 162, an excision target determination unit 163, a highlight information generation unit 164, and a display control unit 165. The processing unit 160 controls each unit of the medical image processing device 100. The processing unit 160 performs processing related to visualization of the tissues. Each unit included in the processing unit 160 may be realized as a different function by one piece of hardware or may be realized as a different function by a plurality of pieces of hardware. Further, each unit included in the processing unit 160 may be realized by a dedicated hardware component.

The region processing unit 161 acquires the volume data of the subject via, for example, the port 110. The region processing unit 161 extracts any region included in the volume data. The region processing unit 161 may automatically designate a region of interest based on, for example, the voxel value of the volume data and extract the region of interest. The region processing unit 161 may manually specify a region of interest and extract the region of interest via, for example, the UI 120. The region of interest may include regions such as the liver, lungs, bronchi, pulmonary arteries, pulmonary veins, portal veins, hepatic veins, and the like. The region of interest may be at least a part of the organ to be excised from the subject. Also, the region of interest may be at least a part of tubular tissues (for example, blood vessels (for example, portal veins, arteries, or veins), bronchi, or bile ducts).

The region processing unit 161 may separate the organ of the subject into segments. The segment may at least roughly coincide with the anatomical segments. The organ may include the liver, kidneys, lungs, and other organs. The segment may be at least a part of the region of the combination of the plurality of segments. The segment may be a subsegment or region smaller than a segment. Voronoi tessellation may be performed in the separation of segments.

The region processing unit 161 may determine the territories of tubular tissues based on the running state of the tubular tissues (for example, arterial territories, portal venous territories, venous territories). For example, the territory region refers to the region nourished by a portal vein or an artery that nourishes (carries nutrients to) a tumor, and venous territories that carry blood from the region. The portal vein or artery that nourishes a tumor is also referred to as a culprit blood vessel. The region processing unit 161 may calculate the territory region by performing Voronoi tessellation using the portal vein or the artery as a seed, for example.

The region processing unit 161 may separate the organ into a plurality of segments by Voronoi tessellation or calculate the territory region. In Voronoi tessellation, the region may be separated into a plurality of segments or the territory region may be calculated based on the distance from the reference line or a point on the line. The reference line may be a line representing the running of tubular tissues such as blood vessels and bronchi.

For example, the region processing unit 161 may separate into the segments or determine the territory region based on the extracted tree structure T1 (for example, a portal vein, an artery, or a bronchus) that tends to run through the center of the segment of the organ. The region processing unit 161 may correct the segment or the territory region resulting from this segmentation based on the edge of the segment or the territory region, or a tree structure T2 (for example, a vein or a lymphatic vessel) that tends to run along the boundary. In addition, the region processing unit 161 may separate the organ into segments or determine the territory region based on the extracted tree structure T1 and tree structure T2. An example of segmentation is disclosed in JP-A-2020-120828.

The region processing unit 161 may calculate the excision region, which is a region to be excised in the organ. The excision region is, for example, a region including a tumor for excising a tumor portion from an organ. The excision region may be the same as or different from the determined territory region. The excision region may be the same as or different from the segment containing the tumor. The region processing unit 161 may manually specify the excision region via the UI 120 or may automatically specify the excision region according to a predetermined algorithm.

The image generation unit 162 generates various images. The image generation unit 162 generates a three-dimensional image or a two-dimensional image based on at least a part of the acquired volume data (for example, the volume data of the extracted region or segment). The image generation unit 162 may generate an image in which a part of the organ included in the excision region is excluded. In this case, the excision region in the organ is excluded, but an image in which at least a part of the tubular tissues in the excision region remains may be generated, or an image in which at least a part of the tubular tissues in the excision region is also excluded may be generated. Further, the image generation unit 162 may generate an image of only the excision region in the organ.

The image generation unit 162 may perform various renderings (for example, volume rendering or surface rendering) to generate an image. The image generation unit 162 may generate an image by using a mask. When a mask is used, the voxels only in the masked region are drawn in the image, and the voxels in the non-masked region are not drawn in the image. In addition, a plurality of masks can be used for each region. Image generation using a mask is disclosed in, for example, JP Patent No. 4188900.

The excision target determination unit 163 determines whether each tubular tissue included in the excision region of the organ is to be excised or not to be excised. That is, each tubular tissue included in the excision region of the organ may or may not be excised together with a part of the organ in the excision region. The specific method for determining whether each tubular tissue included in the excision region of the organ is to be excised or not to be excised will be described later. For example, the tubular tissues not to be excised in the excision region may be a target of image generation by the image generation unit 162, and the tubular tissues to be excised in the excision region may be excluded from the image generation by the image generation unit 162.

The highlight information generation unit 164 generates highlight information for highlighting the excision site (for example, the contour of the tubular tissues on the excision surface or the excision surface itself (inside the contour) of the tubular tissues) of the tubular tissues targeted for excision (for example, a blood vessel or a bronchus). The highlight information includes at least contour highlight information that highlights the contour of the tubular tissues on the excision surface.

The contour highlight information may be a ring formed substantially along the contour of the tubular tissues on the excision surface, or the like. For example, the contour highlight information may include information in which the voxel value of the voxel of the contour of the tubular tissues on the excision surface is made larger than the actually acquired value. The contour highlight information may include information that thickens the contour line of the tubular tissues on the excision surface. The contour highlight information may include information in which the voxels of the contour line are colored differently from those of other voxels adjacent to the contour line.

The highlight information may include surface highlight information that highlights the inside rather than the contour of the excision surface. The surface highlight information may be a shape, pattern, color, fill, and the like inside a ring that outlines the excision surface. For example, the surface highlight information may include information in which the voxel value of the voxel on the surface of the excision surface is larger than the actually acquired value. The surface highlight information may include information in which the voxels on the excision surface are colored differently from those of other voxels adjacent to the excision surface.

The tubular tissues having the excision surface may be tubular tissues to be ligated and resected. Ligation and resection may be performed with tumor removal of the organ, segment excision of the organ, wedge-shaped excision of the organ, and the like. Further, the tubular tissues may be tissues included in an organ (for example, the liver) or lungs. The highlight information may be information that visualizes the direction of the tubular tissues. The highlight information may be generated based on the path of the tubular tissues. The highlight information may be displayed offset from the excision surface. A method of displaying contour highlight information is disclosed in, for example, JP-A-2020-120827.

The display control unit 165 displays various data, information, or images on the display 130. The image includes an image generated by the image generation unit 162. Further, the display control unit 165 superimposes and displays the highlight information on the rendered image.

Figure 3:
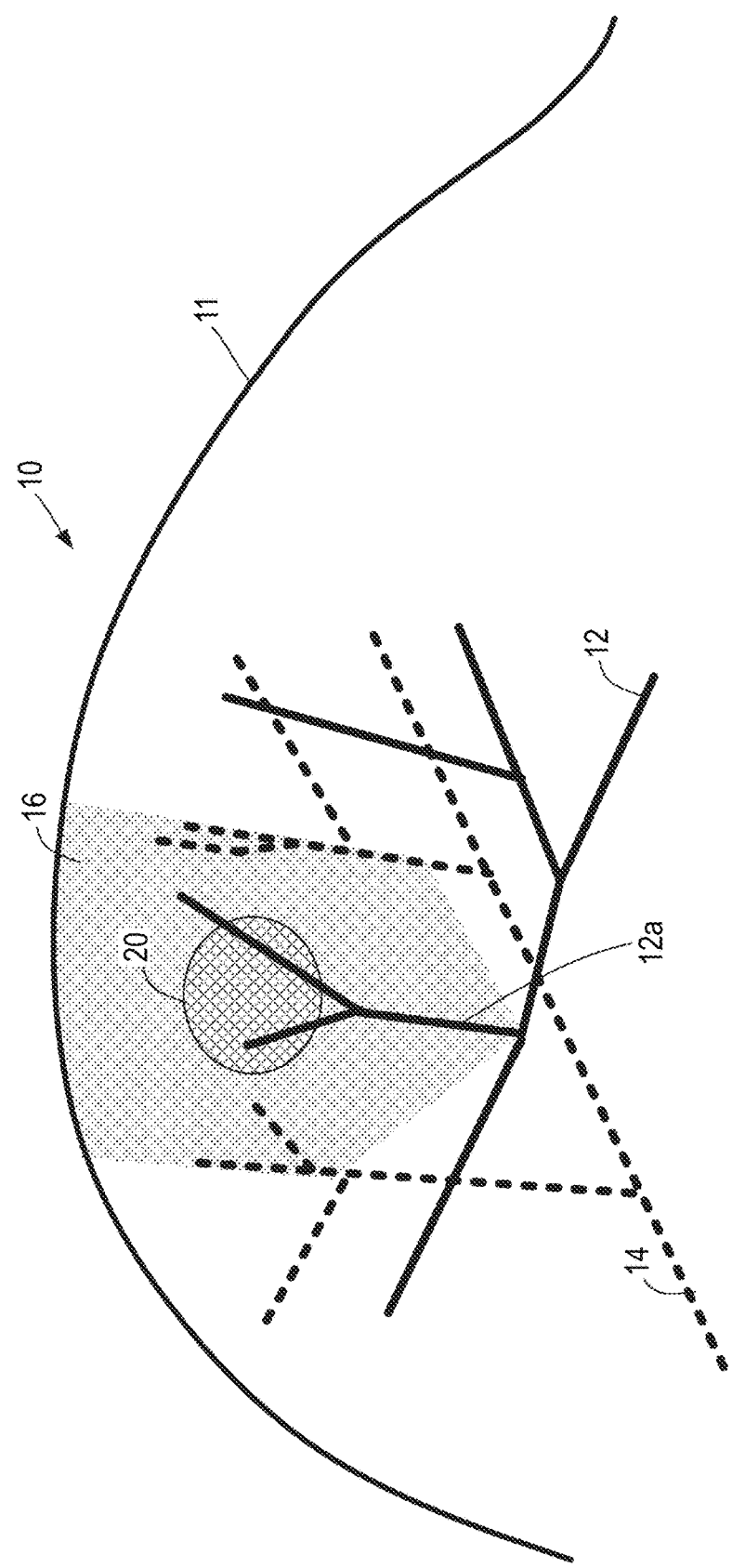
FIG. 3 is a diagram showing an example of a territory region in the liver.

FIG. 3 is a diagram showing an example of a territory region 16 in the liver 10. In FIG. 3, a portal vein 12 and a vein 14 are present inside the surface 11 of the liver 10. A part of the portal vein 12 is a culprit vessel 12a and nourishes the tumor 20. Based on the portal vein 12 including the culprit vessel 12a, the region processing unit 161 determines the territory region 16 which is the region nourished by the culprit vessel 12a by Voronoi tessellation or the like. The region processing unit 161 may determine the territory region 16 by Voronoi tessellation or the like based on the portal vein 12 including the culprit vessel 12a and the vein 14. In FIG. 3, the position of the vein 14 is also considered. Therefore, in FIG. 3, the outer peripheral portion of the territory region 16 is formed with the distances from the plurality of portal veins located close to each other being approximately equidistant. Further, the outer peripheral portion of the territory region 16 is formed along the running of the vein 14.

In FIG. 3, for the explanation, the portal vein 12 is shown by a solid line, and the vein 14 is shown by a dotted line (broken line). The same applies to the subsequent drawings.

Figure 4:
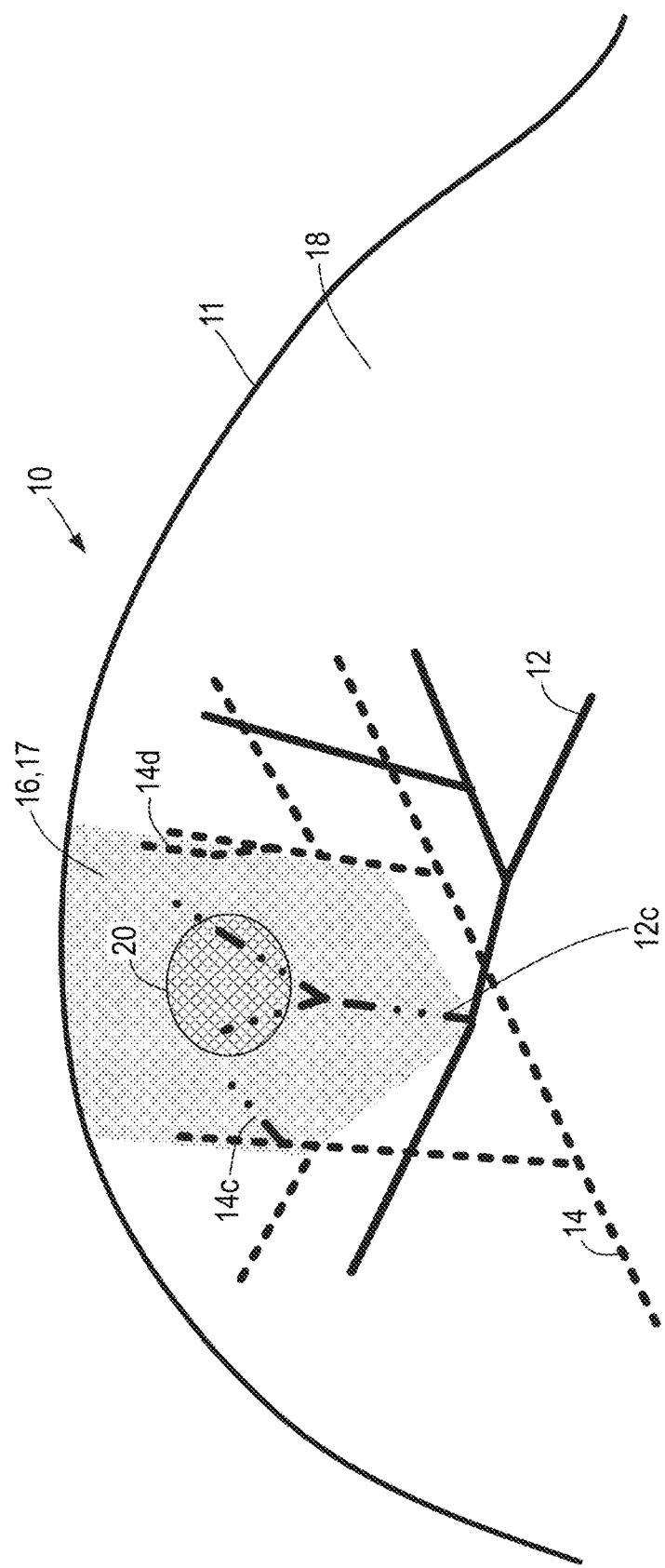
FIG. 4 is a diagram showing an example of an excision region, a residual region, and each blood vessel to be excised or not to be excised in the liver.

FIG. 4 is a diagram showing an example of an excision region 17 and a residual region 18 and each blood vessel to be excised or not to be excised in the liver 10. The excision region 17 is a region of the liver 10 to be excised by partial excision surgery or the like. The residual region 18 is a region in which the excision region 17 is removed from the liver 10, and is a region left as a part of the liver 10 by partial excision surgery or the like. For example, the region processing unit 161 may calculate the excision region 17 based on the territory region 16 or may arbitrarily specify the territory region 16 via the UI 120. Further, a doctor performing the partial excision surgery or the like may operate the UI 120, and the region processing unit 161 may modify a part of the territory region 16 to generate the excision region 17 based on the operation on the UI 120. Further, the territory region 16 may not be modified by the doctor at all via the UI 120, and the territory region 16 and the excision region 17 may be the same region.

In partial excision surgery for organs such as the liver 10, blood vessels attached to the organs can also be excised. For example, the excision target determination unit 163 may determine all the blood vessels (for example, the portal vein 12 or the vein 14) in the excision region 17 as the blood vessels to be excised. The excision target determination unit 163 may determine a part of the blood vessels (for example, the portal vein 12 or the vein 14) in the excision region 17 as the blood vessels not to be excised. For example, among the blood vessels in the excision region 17, the blood vessels along the marginal portion (peripheral end) of the excision region 17 may be determined as the blood vessels not to be excised. In FIG. 4, a portal vein 12c to be excised and a vein 14c to be excised are shown, and a vein 14d not to be excised is also shown.

The vein is likely to be located at the peripheral end of the excision region 17. When this vein is excised, blood may accumulate outside the excision region 17 (i.e., the residual region 18) and some tissues in the residual region 18 may fail. On the other hand, the medical image processing device 100 determines the blood vessels along the marginal portion (peripheral end) of the excision region 17 as the blood vessels not to be excised, so that the deterioration of the function of the unexcised residual region 18 can be reduced.

In FIG. 4, for the explanation, the blood vessel to be excised (for example, a portal vein or a vein) is shown by a two-dot chain line. The same applies to the subsequent drawings.

Figure 5:
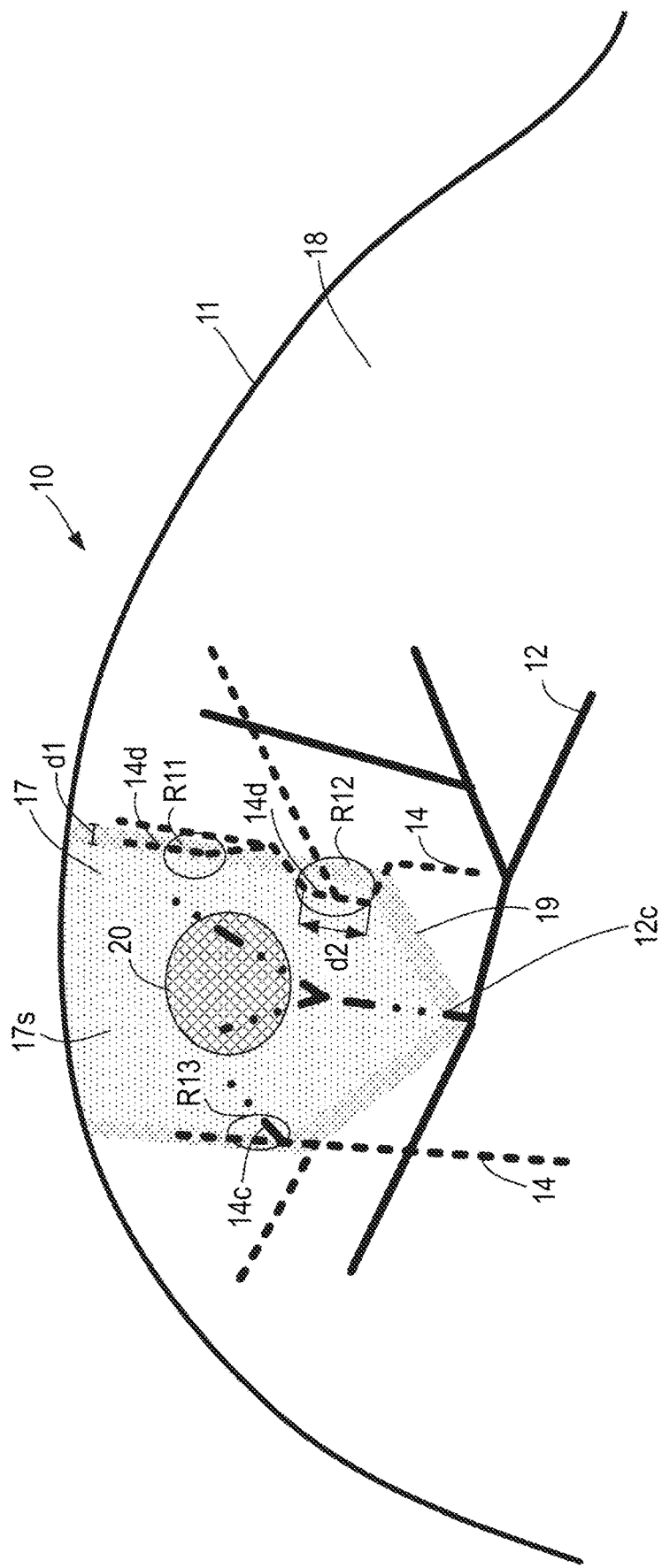
FIG. 5 is a diagram for illustrating a method of determining whether or not to excise a blood vessel in the excision region.

FIG. 5 is a diagram for illustrating a method of determining whether or not to excise the blood vessel in the excision region 17. The excision target determination unit 163 generates a contraction region 17s in which the excision region 17 is contracted (erodes) by a morphological transformation at a predetermined distance. In this case, the peripheral end of the excision region 17 and the peripheral end of the contraction region 17s are separated by a distance d1 (for example, 3 mm).

The excision target determination unit 163 determines the blood vessel that does not enter the contraction region 17s as a blood vessel not to be excised (for example, vein 14d) (see region R11). Further, the excision target determination unit 163 meanders and runs, and even if there is a section that partially enters the contraction region 17s (for example, less than a predetermined length d2 on the blood vessel path), the excision target determination unit 163 determines the blood vessel that quickly exits from the contraction region 17s as a blood vessel not to be excised (for example, vein 14d) (see region R12). The length d2 may be, for example, 10 mm. Further, the excision target determination unit 163 may determine the blood vessel that enters the contraction region 17s and does not exit as a blood vessel to be excised (for example, vein 14c) (see, for example, region R13).

The contraction region 17s used for determining whether or not to be excised may differ depending on the type of blood vessels (for example, portal vein or vein) for which whether or not to be excised is determined. That is, a contraction region 17s1 (not shown) for determining whether the portal vein 12 is to be excised and a contraction region 17s2 (not shown) for determining whether the vein 14 is to be excised may be different. In this case, the excision target determination unit 163 may contract the excision region 17 at different magnifications to generate the contraction regions 17s1 and 17s2.

Reference numeral 19 in FIG. 5 indicates a line on the surface of the liver in which a notch is made when the excision region is excised.

Figure 6:
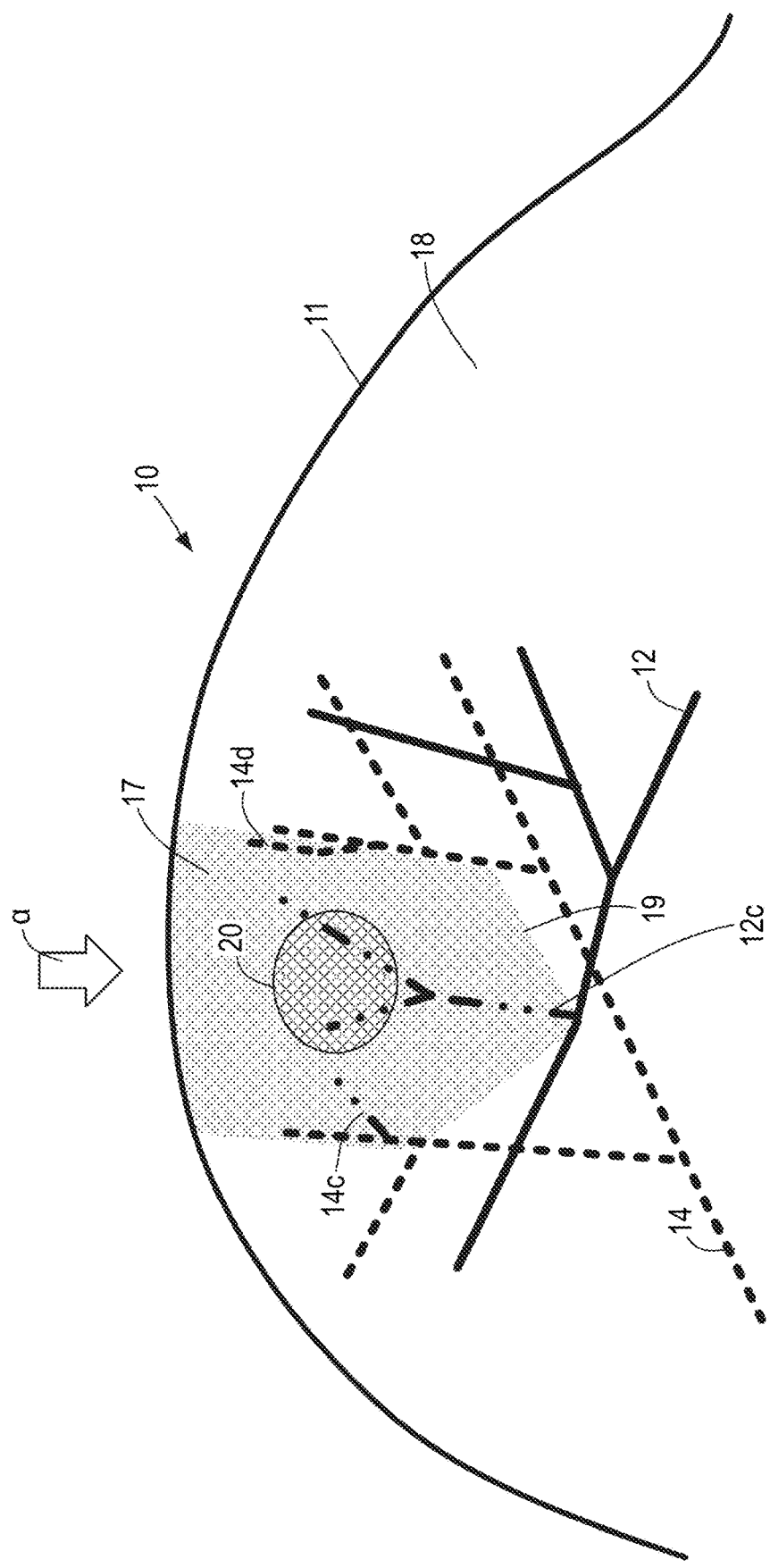
FIG. 6 is a diagram showing an example of the line-of-sight direction α for generating a three-dimensional image.

FIG. 6 is a diagram showing an example of the line-of-sight direction α for generating a three-dimensional image. The image generation unit 162 acquires information on the line-of-sight direction α and generates a three-dimensional image of the subject (for example, around an organ) when the line-of-sight direction α is viewed from the outside of the subject. The line-of-sight direction α may be instructed via, for example, the UI 120 or may be instructed by another method. Therefore, a three-dimensional image that visualizes the entire liver 10 including the excision region 17 may be generated or a three-dimensional image that visualizes the portion excluding the excision region 17 from the liver 10 may be generated. Further, the image generation unit 162 may generate a three-dimensional image that visualizes at least a part of the blood vessels in the excision region 17 or may generate a three-dimensional image that does not visualize at least a part of the blood vessels.

In this way, the image generation unit 162 may or may not set various regions and tissues as targets for generating a three-dimensional image for a target to be partially excised by a simulation of partial excision surgery (also referred to as excision simulation). The display control unit 165 displays the three-dimensional image thus generated for the excision simulation on the display 130. In this case, the site as a target of three-dimensional image generation is the display target and the site as a non-target of three-dimensional image generation is not the display target. The display control unit 165 may specify which site is to be a target of three-dimensional image generation or a display target by, for example, a doctor performing the excision simulation via the UI20.

Figure 7A:
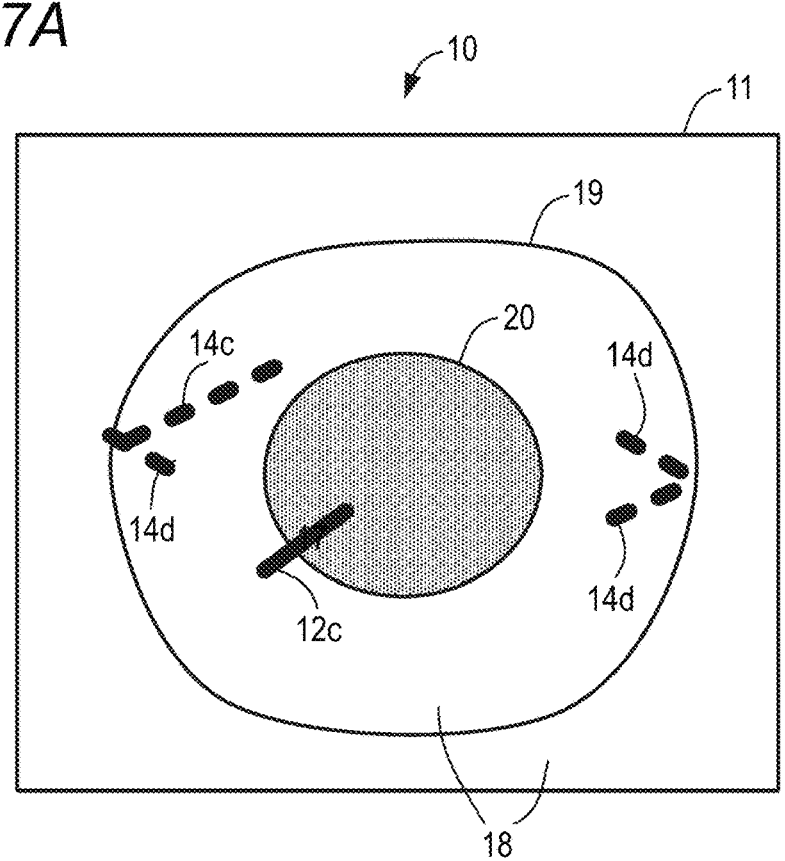
FIG. 7A is a schematic diagram showing a first display example that simplifies a three-dimensional image for excision simulation when the line-of-sight direction α is viewed from the outside of the subject.

FIG. 7A is a schematic diagram showing a first display example in which a three-dimensional image for excision simulation when the line-of-sight direction α is viewed from the outside of the subject is simplified. The image of FIG. 7A is used, for example, to check the relationship between the tumor 20 and the running of each blood vessel. In the case of FIG. 7A, the display control unit 165 designates the excision region 17 as a non-display target, designates the tumor 20 in the excision region 17 as a display target, and designates the portal vein 12c to be excited in the excision region 17 as a display target. Further, the display control unit 165 designates the vein 14c to be excised in the excision region 17 as a display target, designates the vein 14d not to be excised in the excision region 17 as a display target, and designates the residual region 18 as a display target. As a result, in the image of FIG. 7A, each site designated as the display target is displayed and the sites designated as the non-display targets are not displayed.

Figure 7B:
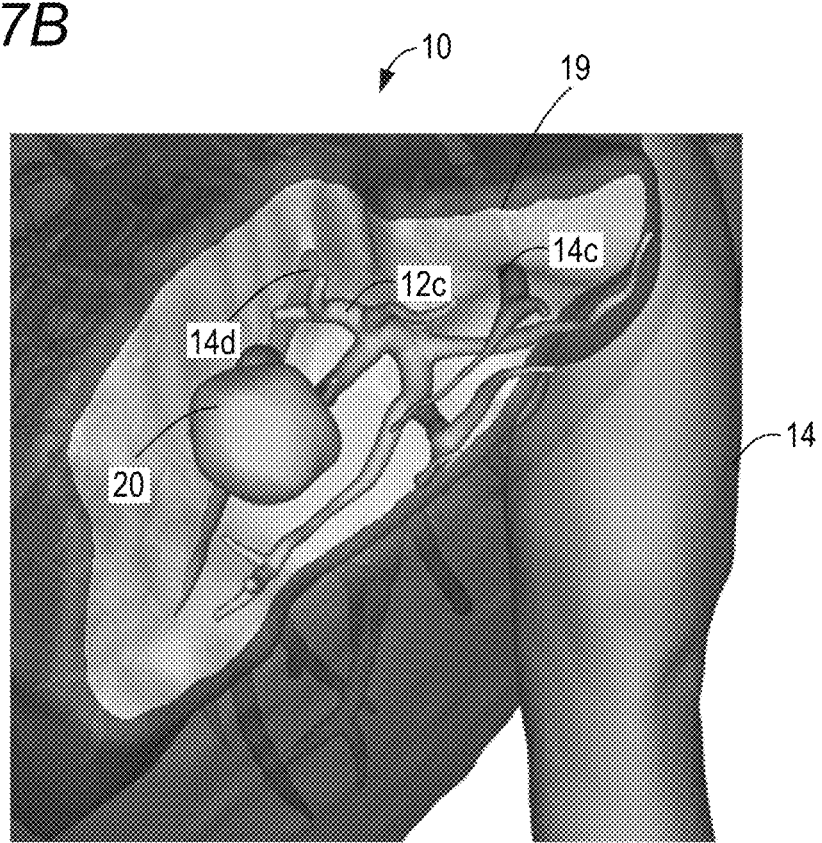
FIG. 7B is a diagram showing a first display example of an actual simulation image of the excision simulation.

FIG. 7B is a diagram showing a first display example of an actual simulation image of the excision simulation. In FIG. 7B, the same site as the display target site in FIG. 7A is the display target and the same site as the non-display target site in FIG. 7A is the non-display target. Further, the surface of the residual region 18 is translucent and some blood vessels in the residual region 18 are also drawn.

Figure 8A:
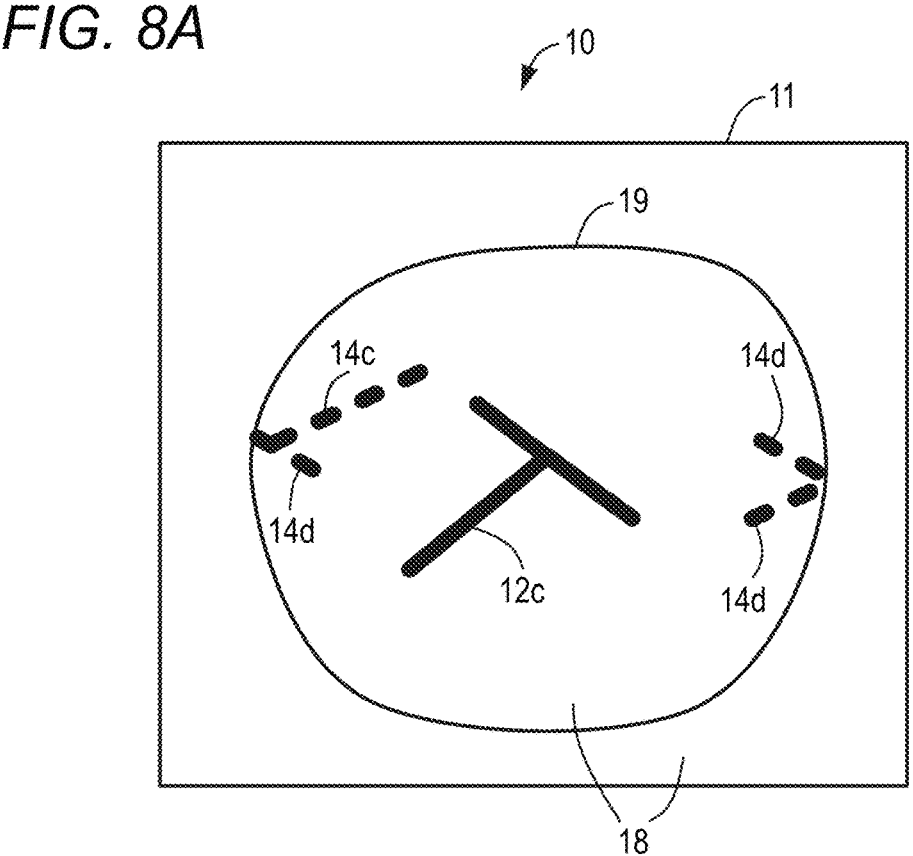
FIG. 8A is a schematic diagram showing a second display example of a three-dimensional image for excision simulation when the line-of-sight direction α is viewed from the outside of the subject.

FIG. 8A is a schematic view showing a second display example of a three-dimensional image for excision simulation when the line-of-sight direction α is viewed from the outside of the subject. The image of FIG. 8A is used, for example, to check the running relationship of each blood vessel. In the case of FIG. 8A, the display control unit 165 designates the excision region 17 as a non-display target, designates the tumor 20 in the excision region 17 as a non-display target, and designates the portal vein 12c to be excised in the excision region 17 as a display target. Further, the display control unit 165 designates the vein 14c to be excised in the excision region 17 as a display target, designates the vein 14d not to be excised in the excision region 17 as a display target, and designates the residual region 18 as a display target. As a result, in the image of FIG. 8A, the sites designated as the display targets are displayed, and the sites designated as the non-display targets are not displayed.

Figure 8B:
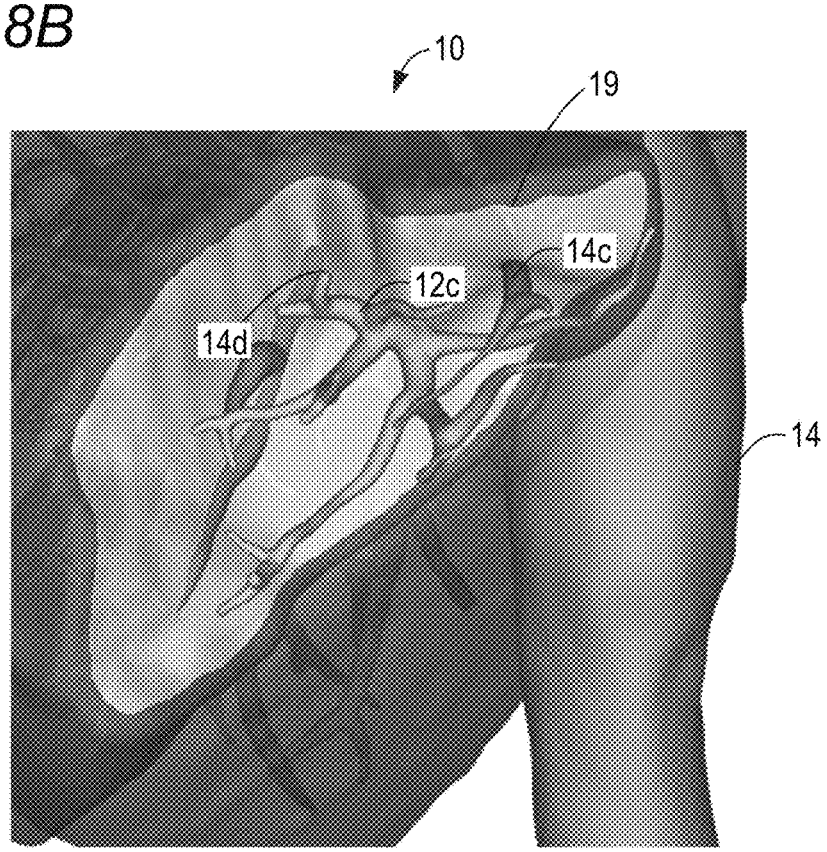
FIG. 8B is a diagram showing a second display example of an actual simulation image of the excision simulation.

FIG. 8B is a diagram showing a second display example of an actual simulation image of the excision simulation. In FIG. 8B, the same site as the display target site in FIG. 8A is the display target and the same site as the non-display target site in FIG. 8A is the non-display target. Further, the surface of the residual region 18 is translucent and some blood vessels in the residual region 18 are also drawn.

Figure 9A:
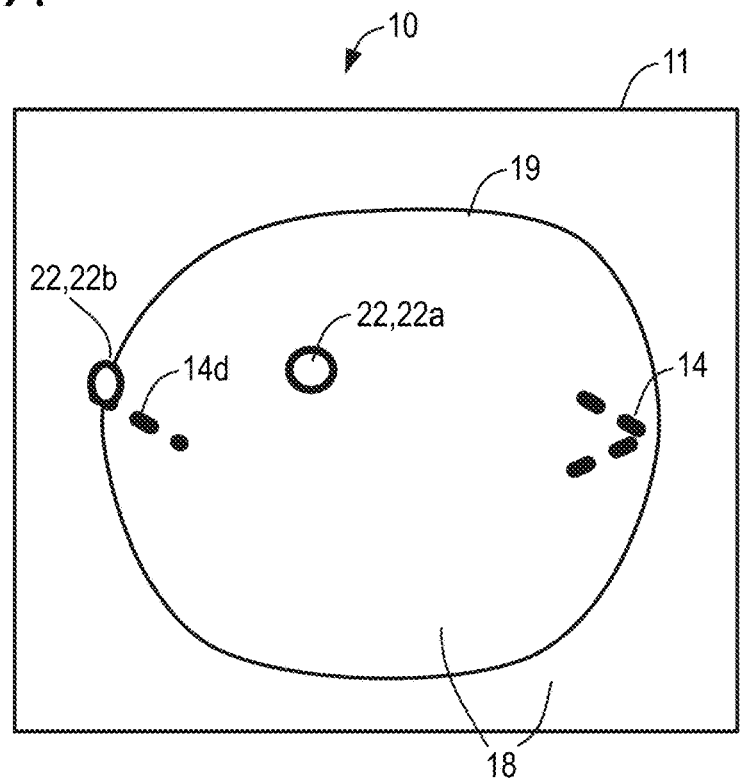
FIG. 9A is a schematic diagram showing a third display example of a three-dimensional image for excision simulation when the line-of-sight direction α is viewed from the outside of the subject.

FIG. 9A is a schematic diagram showing a third display example of a three-dimensional image for excision simulation when the line-of-sight direction α is viewed from the outside of the subject. The image of FIG. 9A is used, for example, for simulating the scene after surgery. In the case of FIG. 9A, the display control unit 165 designates the excision region 17 as a non-display target, designates the tumor 20 in the excision region 17 as a non-display target, and designates the portal vein 12c to be excised in the excision region 17 as a non-display target. Further, the display control unit 165 designates the vein 14c to be excised in the excision region 17 as a non-display target, designates the vein 14d not to be excised in the excision region 17 as a display target, and designates the residual region 18 as a display target. As a result, in the image of FIG. 9A, the sites designated as the display targets are displayed and the sites designated as the non-display targets are not displayed.

Further, in the image of FIG. 9A, the highlight information 22 is displayed. For example, ring-shaped highlight information 22a is displayed for the excision site (for example, the ligation and resection site) where the portal vein 12 is excised. For example, ring-shaped highlight information 22b is displayed for the excision site (for example, the ligation and resection site) where the vein 14 is excised. Further, the surface of the residual region 18 is translucent and some blood vessels in the residual region 18 are also drawn.

Figure 9B:
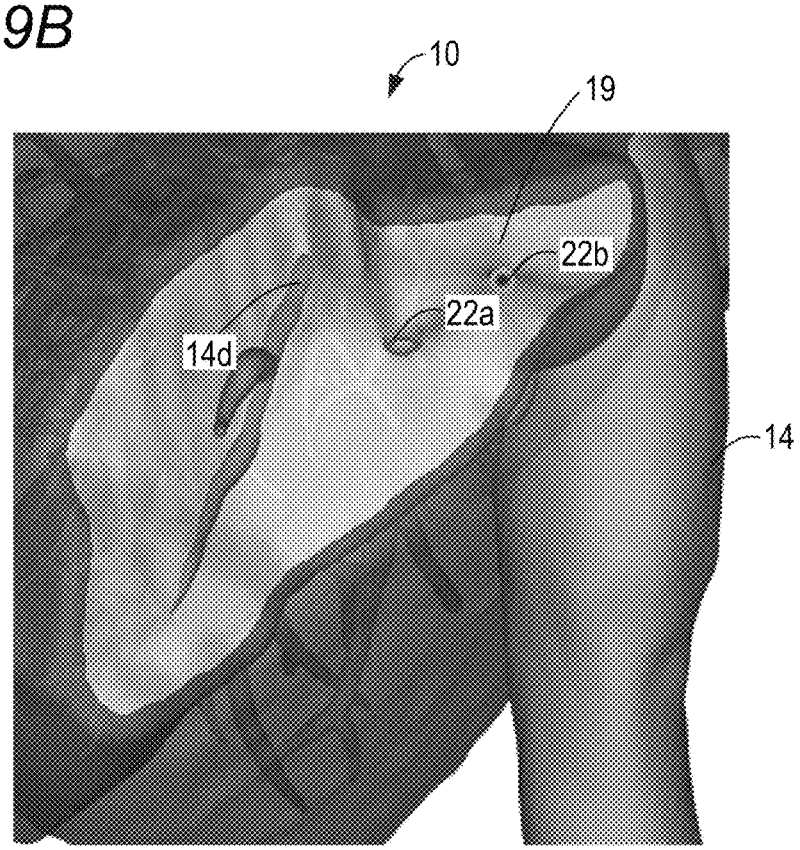
FIG. 9B is a diagram showing a third display example of an actual simulation image of excision simulation.

FIG. 9B is a diagram showing a third display example of an actual simulation image of the excision simulation. In FIG. 9B, the same site as the display target site in FIG. 9A is the display target and the same site as the non-display target site in FIG. 9A is the non-display target.

Figure 10:
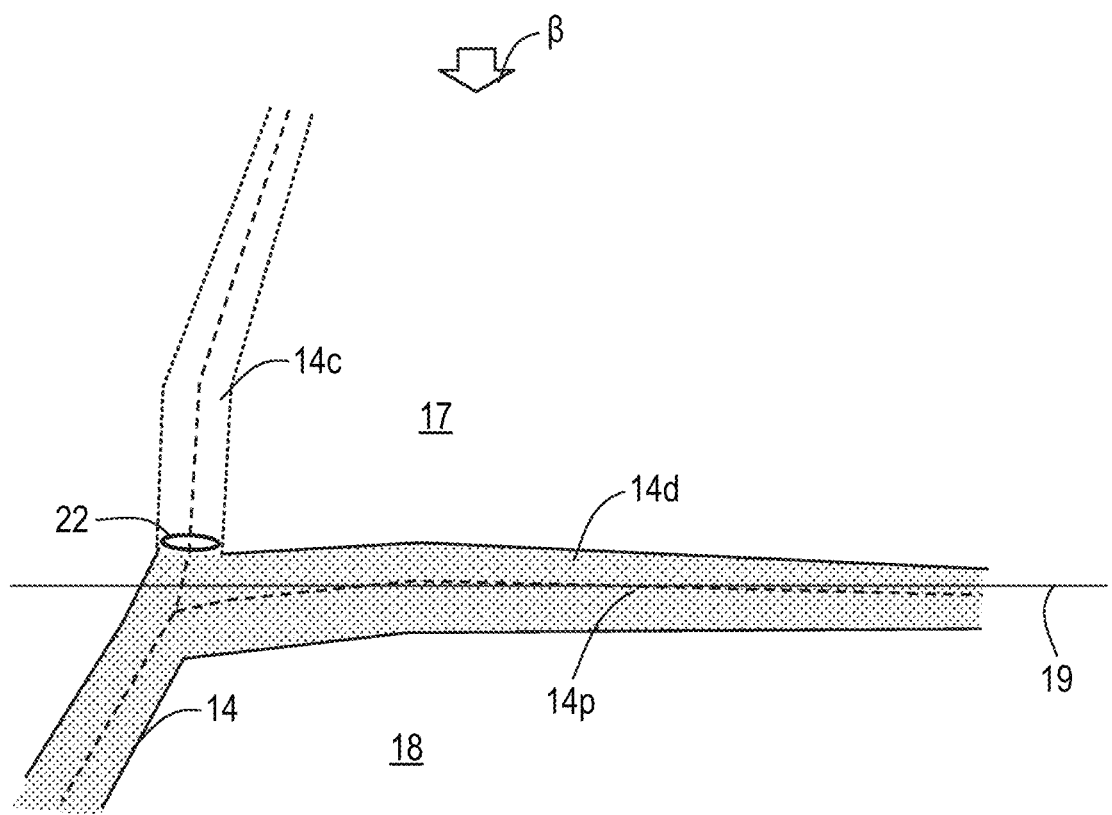
FIG. 10 is a diagram for illustrating a case where a blood vessel runs along the boundary of the excision region.

FIG. 10 is a diagram for illustrating a case where a blood vessel runs along the boundary of the excision region.

The blood vessel may run near the boundary of the excision region 17. For example, in the excision region 17 in which the territory region 16 of the culprit vessel is modified, the vein 14 tends to run on the boundary of the excision region 17. In this case, it is preferable to preserve the vein 14d that affects the residual region 18 between the vein 14c and the vein 14d branched from the vein 14 at the time of the partial excision surgery because the blood circulation of the tissues outside the excision region 17 is improved. Therefore, the excision target determination unit 163 determines the vein 14c running toward the inside of the excision region 17 as an excision target. On the other hand, the vein 14d running on the boundary of the excision region 17 is preserved. In this case, the image generation unit 162 and the display control unit 165 draw the vein 14d running on the boundary of the excision region 17 as an image generation target and set the vein 14d as a display target.

Further, the display control unit 165 displays the highlight information 22 for highlighting the excision site of the vein 14c to be excised at the excision site of the vein 14. In this case, the highlight information generation unit 164 may generate the highlight information 22 based on, for example, the running state of the blood vessel path 14p of the vein 14 corresponding to the excision site of the vein 14.

Therefore, with the boundary surface of the excision region 17 as the boundary, the excision target determination unit 163 may determine the vein 14 included in the residual region 18 outside the boundary of the excision region 17 as a non-excision target, determine the vein 14d running on the boundary of the excision region 17 as a non-excision target, and determine the vein 14c running inside the excision region 17 rather than the boundary of the excision region 17 as an excision target. In this case, the display control unit 165 may designate the vein 14 included in the residual region 18 as a display target. When this is visualized from the line-of-sight direction β, an image as shown in FIG. 9A or FIG. 9B or the like can be obtained. The display control unit 165 may designate the vein 14d running on the boundary of the excision region 17 as a display target. The display control unit 165 may designate the vein 14c running inside the excision region 17 rather than the boundary of the excision region 17 as a display target. Then, the display control unit 165 may display the excision site with the highlight information 22 in the vein 14 running between the outside and the inside of the excision region 17. When this is visualized from the line-of-sight direction β, an image as shown in FIG. 8A or FIG. 8B or the like can be obtained.

Next, an operation example of the medical image processing device 100 will be described.

Figure 11:
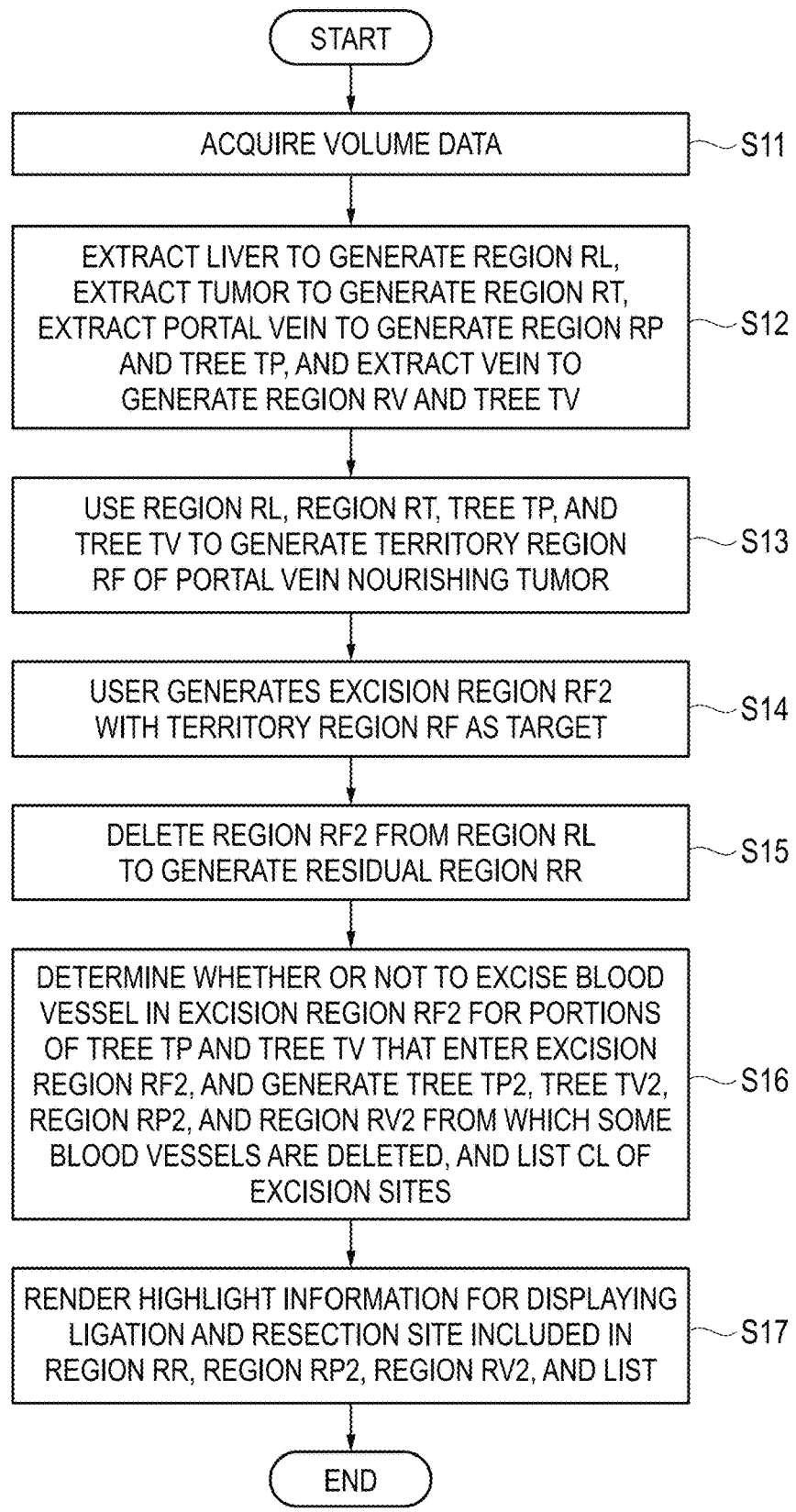
FIG. 11 is a flowchart showing an operation example of the medical image processing device.

FIG. 11 is a flowchart showing an operation example of the medical image processing device 100. The processing of FIG. 11 is performed by, for example, each unit in the processing unit 160.

First, the port 110 acquires volume data including the liver 10 of a subject (S11). The region processing unit 161 extracts the liver 10 from the volume data to obtain a liver region RL, and extracts the tumor 20 to obtain a tumor region RT (S12). The region processing unit 161 extracts the portal vein 12 from the volume data to obtain a portal vein region RP and generates a portal vein tree TP (path tree) as a tree structure of the portal vein 12 (S12). The region processing unit 161 extracts the vein 14 from the volume data to obtain a vein region RV and generates a vein tree TV (path tree) as a tree structure of the vein 14 (S12). The region processing unit 161 generates a territory region RF (corresponding to the territory region 16) of the portal vein 12 nourishing the tumor 20 based on the liver region RL, the tumor region RT, the portal vein tree TP, and the vein tree TV (S13). The UI 120 receives an operation for the territory region RF from the user and sends the operation information to the region processing unit 161. The region processing unit 161 generates an excision region RF2 (corresponding to the excision region RF17) based on the operation information from the UI 120 (S14). The region processing unit 161 deletes the excision region RF2 from the liver region RL to generate a residual region RR (corresponding to the residual region 18) (S15).

The excision target determination unit 163 determines whether or not to excise the blood vessels (for example, the portal vein or the vein) in the excision region RF2 for the portion of the portal vein tree TP and the vein tree TV that enters the excision region RF2 (S16). The region processing unit 161 generates a portal vein tree TP2 in which the portal vein targeted for excision is deleted from the portal vein tree TP (S16). In addition, a vein tree TV2 in which the vein targeted for excision is deleted from the vein tree TV is generated (S16). In addition, a portal vein region RP2 in which the portal vein targeted for excision is deleted from the portal vein region PR is generated (S16). In addition, a vein region RV2 in which the vein targeted for excision is deleted from the vein region PV is generated (S16). In addition, a list CL of the excision sites (a list of locations for displaying ligation and resection sites based on the highlight information 22) is generated (S16). For example, a list of deleted endpoints of the portal vein tree TP2 from which the portal vein 12 targeted for excision was deleted and a list of deleted endpoints of the vein tree TPV from which the vein 14 targeted for excision was deleted are offset by the method of [0043] to [0045] of JP-A-2020-120828 to generate the list CL of the excision sites.

The image generation unit 162 generates a rendered image by rendering the residual region RR, the portal vein region RP2 in which the portal vein targeted for excision was deleted, the vein region RV2 in which the vein targeted for excision was deleted, and the highlight information 22 for displaying the ligation and resection sites included in the list CL (S17). The display control unit 165 displays the rendered image on the display 130 (S17). The image generation unit 162 may render the residual region RR, the portal vein region RP2 in which the portal vein targeted for excision was deleted, and the vein region RV2 in which the vein targeted for excision was deleted to generate a rendered image and the display control unit 165 may superimpose and display the highlight information 22 for displaying the ligation and resection sites included in the list CL on the rendered image.

Further, the processing unit 160 can apply the technique described in JP-A-2016-202319 to the visualization (display) of a plurality of regions (for example, the residual region RR, the portal vein region RP, and the vein region RV2). That is, even when a plurality of regions overlap in the image shown on the two-dimensional display surface, the user can distinguish the plurality of regions by coloring each region.

In partial excision surgery of an organ, the organ is excised for the purpose of extraction of the tumor 20 or segment excision of the organ. As tubular tissues on the excision surface of the organ, there are tubular tissues that are excised, ligated and resected and tubular tissues that remain without being excised. On the other hand, the medical image processing device 100 can distinguish the tubular tissues to be excised and the tubular tissues not to be excised in the excision region 17 of the organ in the excision simulation and display the tubular tissues not to be excised. Therefore, the user can check the blood vessels inside the organ that cannot be actually seen from the outside of the organ at the time of surgery planning, by the surgical simulation. In addition, the medical image processing device 100 can also highlight the ligation and resection planned site when the blood vessel is excised with the partial excision of the organ. This makes it easier for the user to identify the blood vessel to be ligated and resected during surgery planning.

Next, variations of the embodiment will be described.

For example, in the rendering performed by the image generation unit 162, the tumor 20 (region thereof), the residual region 18, and the blood vessels (region thereof) may be volume rendered or surface rendered, or may be a combination of both. For example, the tumor 20 may be volume rendered. The residual region 18 may be surface rendered. The blood vessels (for example, portal vein 12 or vein 14) may be rendered with a combination (mix) of volume rendering and surface rendering. The image generation unit 162 may generate images of various regions by generating masks from volume data or may generate images of various regions by solid or surface. Further, the image generation unit 162 may generate a rendered image by mixing the surface rendering and the volume rendering (see JP-A-2018-121857). Further, the image generation unit 162 may make the boundary of the excision region 17 translucent so that the blood vessel running inside the excision region 17 or inside the residual region 18 can be checked through the boundary. Further, the image generation unit 162 may draw only the shading of the boundary of the excision region 17 so that the blood vessel running inside the excision region 17 or inside the residual region 18 can be checked (see JP-A-2017-189460).

Further, the display control unit 165 may be able to switch between display and non-display of each region in the organ via, for example, the UI 120. In this case, the display control unit 165 may acquire switching information for switching between display and non-display of each region in the organ via, for example, the UI 120 and switch between display and non-display of each region in the organ based on the switching information.

Further, although the display control unit 165 has shown an example in the line-of-sight direction in which the organ is observed through the excision region 17, the line-of-sight direction may be designated in any direction of the user via, for example, the UI 120.

Further, although the partial excision surgery of the organ including the tumor 20 has been mainly exemplified, the excision region 17 may be a region including a disease other than the tumor 20. In addition, the excision region 17 may be a healthy region used as a donor for living organ transplantation. In addition, the UI 120 may include a UI (adjustment UI) to adjust a determination parameter for determining whether each tubular tissue included in the excision region of the organ is to be excised or not to be excised. For example, the adjustment UI may specify the distance to be contracted by the morphological transformation to generate the contraction region 17s from the excision region 17.

Further, the region processing unit 161 may extract the tubular tissues as an independent region separately from the artery, the portal vein 12, and the vein 14. Further, for the artery, the portal vein 12, and the vein 14, determination parameters for determining whether to set each to different excision targets or different non-excision targets may be applied. Further, the UI (adjustment UI) for adjusting the determination parameter for determining whether to be excised or not to be excised may be able to set different determination parameters for the artery, the portal vein 12, and the vein 14. Further, the excision target determination unit 163 can simply set all the artery and the portal vein 12 as an excision target and the vein 14 as a non-excision target by distinguishing the portal vein 12 and the vein 14 from each other by the region processing unit 161, extracting them as independent regions, and determining whether the extracted region itself to be excised or not to be excised. In addition, the excision target determination unit 163 can determine the portal vein 12 as the excision target and determine whether the vein 14 is set to the excision target or the non-excision target based on the determination parameter.

Although various embodiments have been described above with reference to the drawings, it is needless to say that the present disclosure is not limited to such examples. It is clear that a person skilled in the art can consider various modifications or changes within the scope of the claims, and it is understood that they also belong to the technical scope of the present disclosure.

Further, the medical image processing device 100 may include at least the processor 140 and the memory 150. The port 110, the UI 120, and the display 130 may be external to the medical image processing device 100.

Further, it has been exemplified that the volume data as the captured CT image is transmitted from the CT scanner 200 to the medical image processing device 100. Instead, the volume data may be transmitted to a server on a network (for example, an image data server (PACS) (not shown)) and stored so that the volume data is temporarily stored. In this case, the port 110 of the medical image processing device 100 may acquire the volume data from the server or the like via a wired line or a wireless line or acquire the volume data via any storage medium (not shown), when necessary.

Further, it has been exemplified that the volume data as the captured CT image is transmitted from the CT scanner 200 to the medical image processing device 100 via the port 110. This includes the case where the CT scanner 200 and the medical image processing device 100 are substantially combined into one product. It also includes the case where the medical image processing device 100 is treated as a console of the CT scanner 200.

Further, although it has been exemplified that the CT scanner 200 captures an image and generates volume data including information inside the subject, another device may capture an image and generate volume data. Other devices include a magnetic resonance imaging (MRI) device, a positron emission tomography (PET) device, an angiography device, or other modality devices. Moreover, the PET device may be used in combination with other modality devices.

Further, it can be expressed as a medical image processing method in which the operation in the medical image processing device 100 is defined. Further, it can be expressed as a program for causing a computer to execute each step of the medical image processing method.

Outline of the Above Embodiment

One aspect of the above embodiment is the medical image processing device 100 for visualizing tissues, and a medical image processing device for visualizing an organ (for example, the liver 10), and includes the processing unit 160. The processing unit 160 acquires volume data including an organ, extracts tubular tissues included in the organ, designates the excision region 17 that is a region to be excised in the organ, and determines whether or not tubular tissues included in the excision region 17 is to be excised, and does not display tubular tissues to be excised in the excision region 17 and displays tubular tissues not to be excised in the excision region 17 on a display unit (for example, display 130) when displaying the residual region 18 that is a range excluding the excision region 17 in the organ.

As a result, the medical image processing device 100 can distinguish between the tubular tissues to be excised and the (remaining) tubular tissues not to be excised when performing partial excision of the organ and determine whether to display or not to display the tubular tissues. Therefore, the medical image processing device 100 can visualize the tubular tissues not to be excised, which is useful information at the time of partial excision surgery of an organ and can perform an accurate surgical simulation, and eventually, it is possible to prevent accidental excision of the tubular tissues to be preserved at the time of surgery. Therefore, the medical image processing device 100 can suitably visualize a state at the time of partial excision of an organ including the state of the tubular tissues in the excision region 17 of the organ.

The tubular tissues may also include at least one type of tubular tissue among the artery, the portal vein 12, and the vein 14. Thereby, for example, when performing partial excision surgery of the liver 10, the medical image processing device 100 can suitably determine which blood vessel (for example, the artery, the portal vein 12, or the vein 14) is to be excised. Therefore, the user can visually recognize the portal vein 12 and the vein 14 that are not to be excised and can easily perform an accurate surgical simulation.

Further, the tubular tissues may contain at least two types of tubular tissues among the artery, the portal vein 12, and the vein 14. Then, the processing unit 160 may extract at least two types of tubular tissues among the tubular tissues separately. As a result, it is possible to perform a surgical simulation for the tubular tissue in the excision region 17, which is handled differently depending on the type at the time of surgery.

Further, the processing unit 160 may determine to excise one type of tubular tissue out of at least two types of tubular tissues and not to excise the other one type of tubular tissue. Thereby, the display and non-display of the tubular tissues in the excision region 17 can be easily determined according to the types of the tubular tissues.

Further, the processing unit 160 may display the region of the tumor 20 included in the excision region 17. Thereby, the medical image processing device 100 can check the state of the tumor 20 which is difficult to see from the outside of the organ. In addition, the user can easily grasp the positional relationship between the tubular tissues not to be excised in the excision region 17, and the tumor 20.

Further, the processing unit 160 may highlight and display the excision site of the tubular tissues to be excised. For example, the processing unit 160 can highlight and display the excision site of the tubular tissues to be excised by the highlight information 22. Therefore, by checking the highlighted display, the user can easily grasp, for example, the positional relationship between the peripheral end of the excision region 17 of the organ and the excision site, and can suitably assist the ligation and resection procedure at the excision site performed as needed.

Further, the processing unit 160 may perform surface rendering or volume rendering on at least one of the organ and the tubular tissues to generate a rendered image and display the rendered image. For example, the tumor 20 may be volume rendered. The residual region 18 may be surface rendered. The blood vessels (for example, portal vein 12 or vein 14) may be rendered with a combination (mix) of volume rendering and surface rendering. As a result, the medical image processing device 100 can perform a display suitable for observing each site to be displayed, for example, it is possible to easily grasp the inside of the tumor in detail, it is possible to easily check the surface of the residual region 18, and it is possible to easily check both the inside and the outer peripheral portion of the blood vessel in a well-balanced manner.

One aspect of the above embodiment may be a medical image processing method for visualizing an organ. The medical image processing method includes acquiring volume data including an organ, extracting tubular tissues included in the organ, designating the excision region 17 that is a region to be excised in the organ, determining whether or not to excise tubular tissues included in the excision region 17, and not displaying tubular tissues to be excised in the excision region 17 and displaying tubular tissues not to be excised in the excision region on a display unit, when displaying the residual region that is a range excluding the excision region 17 in the organ.

One aspect of the embodiment may be a medical image processing program for causing a computer to execute the above medical image processing method.

The present disclosure is useful for a medical image processing device, a medical image processing method, a storage medium storing a medical image processing program, and the like that can suitably visualize a state of an organ at the time of partial excision including the state of tubular tissue in the excision region of the organ.

The invention claimed is:

1. A medical image processing device for visualizing an organ, comprising:
 a processor, wherein the processor is configured:
  to acquire volume data including the organ;
  to extract a tree structure of tubular tissues included in the organ;
  to designate an excision region that is a region to be excised in the organ;
  to determine whether or not to excise tubular tissue portions of the tree structure included in the excision region; and
  not to display tubular tissue portions of the tree structure to be excised in the excision region, and to display tubular tissue portions of the tree structure not to be excised in the excision region on a display unit, when displaying a remaining region that is a range excluding the excision region in the organ.

2. The medical image processing device according to claim 1, wherein the tubular tissues includes at least one type of tubular tissue among an artery, a portal vein, and a vein.

3. The medical image processing device according to claim 1, wherein
 the tubular tissues includes at least two types of tubular tissues among the artery, the portal vein, and the vein, and
 the processor is configured to extract the at least two types of tubular tissues among the tubular tissues separately.

4. The medical image processing device according to claim 3, wherein the processor is configured to determine to excise one type of tubular tissue out of the at least two types of tubular tissues and determines not to excise the other one type of tubular tissue.

5. The medical image processing device according to claim 3, wherein the processor is configured to determine whether or not to excise tubular tissue with different conditions for the at least two types of tubular tissues.

6. The medical image processing device according to claim 1, wherein the processor is configured to display a tumor region included in the excision region.

7. The medical image processing device according to claim 1, wherein the processor is configured to highlight and display an excision site of the tubular tissues to be excised.

8. The medical image processing device according to claim 1, wherein the processor is configured to
 perform surface rendering or volume rendering on at least one of the organ and the tubular tissues to generate a rendered image, and
 display the rendered image.

9. A medical image processing method for visualizing an organ, comprising:
 acquiring volume data including the organ,
 extracting a tree structure of tubular tissues included in the organ,
 designating an excision region that is a region to be excised in the organ,
 determining whether or not to excise tubular tissue portions of the tree structure included in the excision region, and
 not displaying tubular tissue portions of the tree structure to be excised in the excision region and displaying tubular tissue portions of the tree structure not to be excised in the excision region on a display unit, when displaying a residual region that is a range excluding the excision region in the organ.

10. A computer-readable non-transitory storage medium storing a medical image processing program for causing a computer to execute the medical image processing method according to claim 9.

* * * * *